United States Patent
Porzelt et al.

(10) Patent No.: US 8,209,777 B2
(45) Date of Patent: Jul. 3, 2012

(54) HEARING PROTECTION FOR USE IN MAGNETIC RESONANCE FACILITIES

(75) Inventors: Klaus Porzelt, Nürnberg (DE); Daniel Weiß, Nürnberg (DE); Josef Ziegelbauer, Hetzles (DE)

(73) Assignee: Siemens Aktiengesellschaft, München (DE)

( * ) Notice: Subject to any disclaimer, the term of this patent is extended or adjusted under 35 U.S.C. 154(b) by 999 days.

(21) Appl. No.: 11/295,130

(22) Filed: Dec. 6, 2005

(65) Prior Publication Data

US 2006/0123527 A1  Jun. 15, 2006

(30) Foreign Application Priority Data

Dec. 10, 2004  (DE) .......................... 10 2004 059 678

(51) Int. Cl.
*A42B 1/06* (2006.01)
(52) U.S. Cl. ............................................. 2/209
(58) Field of Classification Search ............... 381/383, 381/371, 374, 370; 2/209, 423
See application file for complete search history.

(56) References Cited

U.S. PATENT DOCUMENTS

| 2,782,423 | A | * | 2/1957 | Eli Simon et al. ............... 2/209 |
| 2,802,214 | A | * | 8/1957 | Hanks ............................. 2/209 |
| 3,944,018 | A | * | 3/1976 | Satory ........................... 181/175 |
| 4,103,359 | A | * | 8/1978 | Rieppel et al. ................... 2/8.1 |
| 5,500,958 | A | * | 3/1996 | Falco .............................. 2/209 |
| 5,920,911 | A | * | 7/1999 | Cushman ........................ 2/209 |
| 6,418,565 | B1 | * | 7/2002 | Tsujino ........................... 2/425 |
| 6,654,966 | B2 | * | 12/2003 | Rolla .............................. 2/209 |
| 6,854,466 | B2 | * | 2/2005 | Lindgren ...................... 128/864 |
| 2004/0064028 | A1 | | 4/2004 | Deimling | |

FOREIGN PATENT DOCUMENTS

| DE | 82 06 723 U1 | 7/1982 |
| DE | 33 12 801 A1 | 10/1984 |
| DE | 695 13 502 T2 | 7/1995 |
| DE | 102 45 487 A1 | 4/2004 |
| GB | 860030 | 2/1961 |
| WO | WO 02/060365 A1 | 8/2002 |

* cited by examiner

*Primary Examiner* — Tejash Patel

(57) ABSTRACT

A hearing protection for use in magnetic resonance facilities, comprising two protective covers for covering the ears of an examination patient, said covers being connected to each other via a clip, wherein each cover has a plastic outer shell, wherein a compact inner part is arranged in and permanently connected to the outer shell, said inner part consisting of a dimensionally stable plastic mass and essentially filling the outer shell completely.

13 Claims, 2 Drawing Sheets

HEARING PROTECTION FOR USE IN MAGNETIC RESONANCE FACILITIES

CROSS REFERENCE TO RELATED APPLICATION

This application claims priority of the German application No. 10 2004 059 678.6 DE filed Dec. 10, 2004, which is incorporated by reference herein in its entirety.

FIELD OF THE INVENTION

The invention relates to a hearing protection for use in magnetic resonance facilities, comprising two protective covers for covering the ears of an examination patient, said covers being connected to each other via a clip, wherein each cover has a plastic outer shell.

BACKGROUND OF THE INVENTION

During the operation of a magnetic resonance facility, a perceptible noise pattern is known to occur as a result of the operating technology. Consequently, an examination patient who is examined using a magnetic resonance facility must wear a hearing protection, wherein this must ensure that the loudness level does not exceed 99 bBa at the ears of the patient.

A known hearing protection which is often also called capsule hearing protection consists of two ear covers which normally fit closely onto the ear, or onto the head around the ear, over padding. The covers are connected together via a clip, which can be telescoped such that the hearing protection can be adapted to the head size, and are usually pivotably attached to the clip. Known covers consist of an almost semispherical or domed plastic shell which is curved outwards and inside which a thin foam inlay is arranged, wherein the annular ear padding is arranged in the area facing the head. The curvature of the mainly oval outer shell is usually not symmetrical, said outer shell instead curving further outwards in the lower section, which is further from the clip, than in the upper section. The shell itself encompasses a relatively large volume which is sealed relative to the head via the ear pad. The attenuation is primarily due to the fact that a relatively large volume is encapsulated via the outer shell. The internal foam part contributes little to the actual noise attenuation and serves primarily to attenuate the perception of the noise of the blood.

Such a hearing protection having a construction of considerable width can be used for a range of examinations in magnetic resonance facilities because there are no space problems. In the case of examinations in the head and neck area, however, special surface coils called head coils or head-neck coils must be positioned next to the patient in order to allow the recording of meaningful magnetic resonance images. The coils, which are normally designed in the form of a cage, must be arranged as close as possible to the head of the patient in this case. A hearing protection of the type cited at the beginning cannot be used in such cases since said hearing protection often cannot be properly applied or the coils cannot be properly positioned. Consequently, use is often made of simple foam covers which can be placed over the ears of the patient and pushed underneath the head coil or head-neck coil. The sound protection that can be achieved hereby is relatively modest and the noise stress of the patient is therefore high.

The German utility model DE 82 06 723 U1 discloses a hearing protection shell, wherein an attenuating inlay is fastened in the shell by means of a retainer ring, wherein the retainer ring and the shell part are connected together by means of a snap-on arrangement. A sound-absorbing material is provided as an attenuating inlay.

DE 33 12 801 A1 discloses a hearing protection device which additionally includes built-in electromechanical components for generating signals which are similar to a heart rhythm. A sound-absorbing elastic material, in particular foam rubber, is proposed as a noise protection inlay in this case. Nothing is disclosed in relation to the fastening of the noise protection inlay.

The British patent specification GB 860,030 discloses a hearing protection device whose hearing protection earpiece can be adjusted in its orientation. It is also mentioned here that the earpieces can preferably be filled with a noise-attenuating material such as plastic foam or foam rubber.

The international patent application WO 02/060365 A1 discloses a method for producing a hearing protection earpiece. In this case, it is again proposed that provision be made for a foamed noise-attenuating plastic material within the earpiece.

DE 695 13 502 T2 is concerned with a disc connection for a hearing protector, wherein a sealing disc can be attached to the hearing protection earpiece in a simple and re-releasable manner and taken off again. The sealing cushion element of a capsule hearing protection is therefore exchangeable. The manner in which the noise attenuation occurs is not described.

A head fixing apparatus for an imaging medical examination device is described in DE 102 45 487 A1. In this case, the fixing cushions are shaped so as to form a chamber that encloses an ear when they are fixed. Sound is pneumatically transferred into this chamber via an air duct.

The invention therefore addresses the problem of specifying a hearing protection which, even in the case of examinations involving head coils and head-neck coils, can readily be used and integrated in the coil, and which offers an adequate sound protection at the same time.

In order to solve this problem in the case of a hearing protection of the type cited at the beginning, provision is made for a compact inner part to be arranged in and permanently connected to the plastic outer shell, said inner part consisting of a dimensionally stable plastic mass and essentially filling the outer shell completely.

SUMMARY OF THE INVENTION

The aim is to significantly reduce the lateral construction space of a cover, thereby however effecting a significantly smaller-shell volume. But since only a restricted shell volume will therefore be available in comparison with known shells of semispherical or domed design having considerable width and outward curvature, the actual attenuation effect however depending particularly on a large encapsulated volume in the case of a known hearing protection, provision must be made for means which ensure adequate sound attenuation in spite of limited volume and limited lateral structure of the outer shell. In order to achieve this, the invention provides for an inner part which is arranged in and permanently connected to the plastic outer shell, said inner part consisting of a dimensionally stable plastic mass and essentially filling the outer shell completely. Therefore the outer shell can be either completely filled by the inner part as far as the shell edge, or merely filled to a large extent, wherein e.g. an offset or an edge section facing the ear might remain clear and serve to include a cover, for example. The plastic inner part, whose surface which contacts the outer shell preferably corresponds to the inner surface contour of the outer shell such that it can be positively inserted in a custom-fit manner, is a heavy compact plastic element which should be embodied as densely as possible, if possible from a solid material or including a minimal amount of aerating agent during the manufacturing process of the inner part, primarily by coating or injection molding, in order to achieve a minimal pore volume or a maximal density and weight. In accordance with the invention, it has been shown that an excellent attenuation effect can be achieved if the shell volume is filled by a pure mass element of this type. As a result of this total mass which—apart from an ear pad which is obviously also provided in the claimed hearing protection—is arranged directly adjacent to the ear of the patient, an excellent attenuation becomes possible since the approaching sound waves can barely penetrate the "mass block". In accordance with the invention, the attenuation is therefore achieved by means of a mass block instead of a large volume.

According to the invention, therefore, it is possible to design the structural shape of the outer shell and therefore the overall cover in accordance with the actual needs. The outer shell—viewed from the front—can be very narrow in design, whether this applies to only a section, e.g. to the lower section which is overlapped by a head-neck coil, or to both a lower and an upper section, or to its whole length, according to requirements. A significant curvature, such as that which was previously crucial, is specifically not required and the outer shell can be essentially plane instead. This is because, as a result of the mass block "filling", a very good attenuation can be achieved even in the case of very small shell volumes. A shell depth of less than 1 cm is possible in some cases.

Since positioning difficulties arise when using a head-neck coil in particular, it is effective and adequate in the case of most applications if, in a completely new type of structural shape, the outer shell has a lower section which is very narrow when viewed from the front and essentially plane when viewed from the side, and which can readily be overlapped by the head-neck coil that extends in the area between the ears and the neck. Adjoining this is an upper section which is wider—viewed from the front—and close to the clip, but is likewise dimensioned such that it can readily be integrated in a normal head coil that surrounds the whole head. This means that the space which is normally available in the upper area is utilized by means of the wider upper section into which more mass can be fitted.

In order optimally to utilize the limited outer shell volume and incorporate as much plastic mass as possible using the inner part, provision should be made for a positive fit between the inner part and the outer shell. In order to achieve a permanent connection, the outer shell can be bonded to the inner part by means of an adhesive layer, for example, wherein it is necessary to ensure a compatibility of the adhesive such that it does not result in an artifact in the magnetic resonance image. It is particularly expedient if the outer shell and the inner part are welded together, this being easily possible in the case of plastic elements. Alternatively, the outer shell can also be coated onto the previously manufactured inner part, such that both undergo an intimate bond. Of course, the inner part can also be injected into the outer shell.

In particular, in order to allow welding together or encapsulation of the two parts, it is advantageous if the outer shell and the inner part are made of the same plastic. In the case of welding, use can be made of a solvent which dissolves the contacting surfaces of the inner part and the outer shell in such a way that they can intimately bond together. Encapsulation is also readily possible in this case.

Since the hearing protection is used in the context of an imaging method, and is moreover arranged in an area in which images will be recorded, it is important in each case to ensure that the hearing protection causes as few image artifacts as possible. For this reason, the whole of the hearing protection must be manufactured from plastic, i.e. not just in the area of the covers, but also in the area of the clip. Any plastic which exhibits the smallest possible magnetic susceptibility, even in the case of larger volumes, is suitable for this purpose. Suitable plastics are already used for manufacturing various components of a magnetic resonance facility and other parts which are utilized in the context of such a facility, particularly the local coils. These plastics can also be used for manufacturing the hearing protection in accordance with the invention. A polycarbonate or a polystyrene is particularly suitable with respect to low susceptibility, wherein these substances not only offer good elasticity (necessary for the head clip) and good durability and processibility, but are also non-magnetic, electrically non-conductive, biocompatible and therefore do not cause skin irritations or similar, and are not readily flammable. A suitable polycarbonate material is that marketed under the trade name "PC Lexan 920 A weiβ" from the company General Electric Plastics, for example, or the polystyrene which is marketed under the trade name "PS Edistir" from the company EniChem can be used. However, this list is not exhaustive.

As previously described, each cover is pivotably connected to the clip for precise adjustment to the shape of the head. In the case of the claimed hearing protection, the pivot joint is advantageously implemented by means of pivot pins which project from and are molded onto the outer shell and on which a holding fork on the clip side is supported in a hinged manner.

It is frequently desirable to be able to offer music or other entertainment as a diversion for the patient, primarily for relaxation or even to prevent claustrophobia during the MR examination. Furthermore, it is frequently necessary during the examination to be able to give the patient instructions in respect of specific activities to be performed by the patient (e.g. inhale, exhale, hold breath, etc.). Therefore there must be a means of communicating with the patient. In order to achieve this, the invention provides for a connector for an acoustic tube at—viewed from the front—the front or rear end face of the outer shell, said connector being connected to a duct which passes through the inner part and leads to the inner part surface that faces the ear of the examination patient. The positioning of the acoustic tube connector at the front or rear end face in accordance with the invention allows a simple tube management even if coils are in place.

In this case, it is particularly effective if one of the pivot pins, which project at the front and rear end face, is hollow and forms the connector. This means that one of the pivot pins has a dual function, serving both as a hinge support for the holding fork and as an acoustic tube connector which can most easily be pushed into and clamped to the hollow pivot pin that is open to the exterior. The pivot pin leads to a duct which passes through the inner part in such a way that the patient can readily be exposed to sound. The duct itself preferably leads to a cavity in the surface of the inner part, said cavity being funnel-shaped, thereby producing a sound funnel via which the sound waves which are supplied via the tube can spread and be supplied to the ear of the patient.

Although it is already possible to achieve a relatively good clarity of the acoustic information in this way, a particularly advantageous configuration of the invention provides for the insertion of a vibrating membrane which is opposite the duct opening or the cavity and exposed to the ear of the examination patient. This vibrating membrane, which is preferably a plastic film, is made to vibrate by the approaching sound waves and communicates this into the volume behind it. In this way, the sound pressure which is produced by the air column in the acoustic tube can be amplified and converted even more effectively, such that the perceptibility of the supplied acoustic information is even better. The vibrating membrane is preferably arranged on the ear pad which is permanently connected to the inner part. The ear pad itself preferably has a stable mounting which has a perforation, wherein said perforation corresponds to the duct opening or the cavity and is covered by the vibrating membrane that is connected to the mounting. By utilizing this mounting, not only is adequate stability provided for the ear pad, but the ear pad itself can also be cleaned effectively after use, since a surface is provided which is closed to the opening or the duct. The vibrating membrane can also be readily positioned and fixed in this way. In order to attach the ear pad to the inner part, it is suitably adhered firmly to the inner part via the mounting.

BRIEF DESCRIPTION OF THE DRAWINGS

Further advantages, features and details of the invention are derived from the exemplary embodiment which is described below and with reference to the drawings, in which.

DETAILED DESCRIPTION OF THE INVENTION

Figure 1:
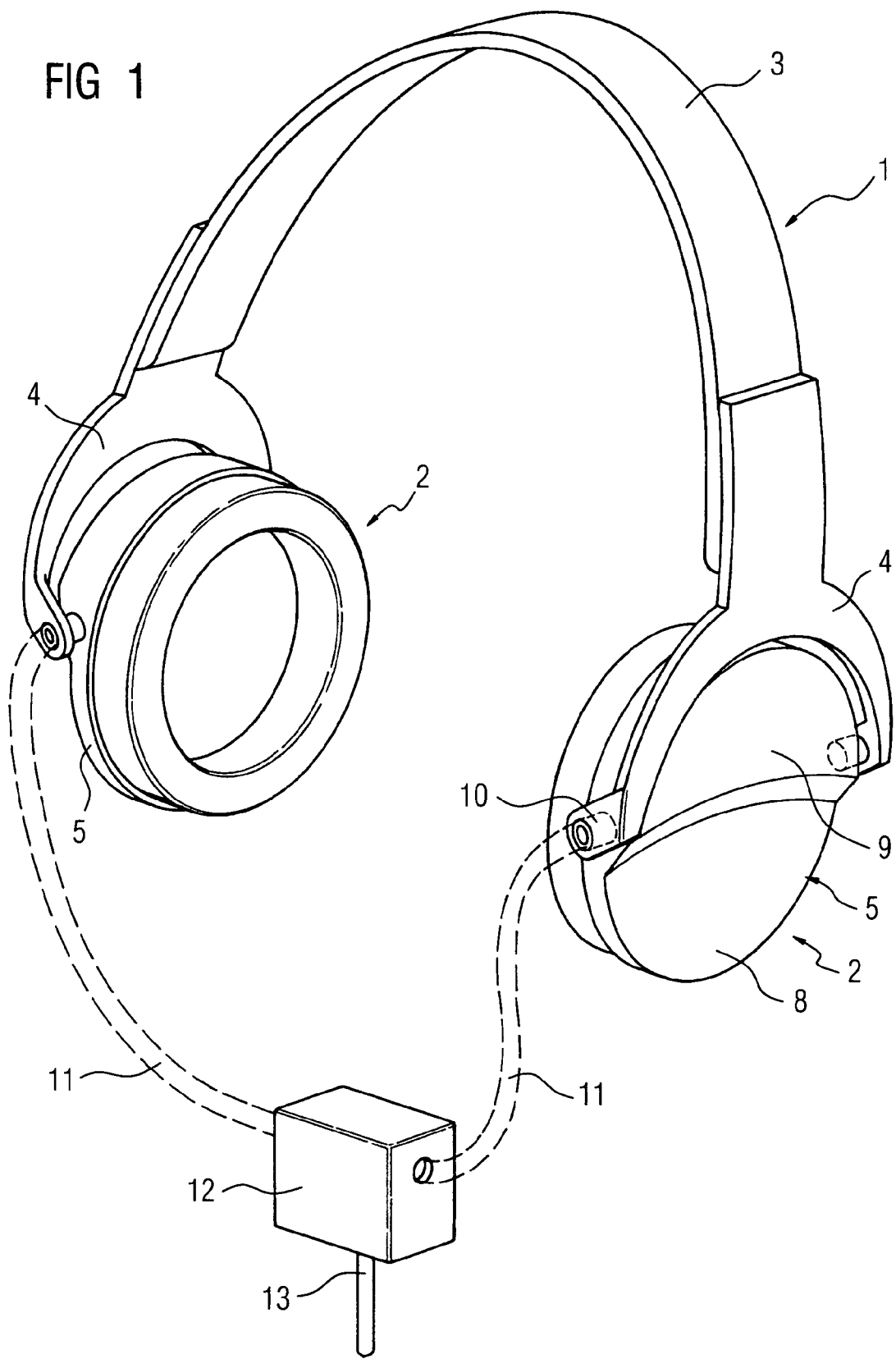
FIG. 1 shows a perspective representation of a hearing protection according to the invention.

FIG. 1 shows a perspective view of the claimed hearing protection 1 which consists of two covers 2 connected via a clip 3 that can be telescoped, said clip having two lateral holding forks 4 and being pivotably connected to the covers 2. Each cover 2 consists of a plastic outer shell 5 containing—see FIG. 2—an integrated inner part which is connected in a positive and custom-fit and permanent (non-detachable) manner and is described in further detail below. The cover 2 also has an ear pad 7 which is attached to the inner part 6 and which is likewise described in further detail.

In order to allow a use of the hearing protection 1 in connection with a head coil or in particular a head-neck coil, each cover 2 and the relevant plastic outer shell 5 is shaped in a special manner in respect of its geometry. It has a lower section 8 which is remote from the clip and—seen in a front view as shown approximately in FIG. 1—is essentially narrower than the rear section 9 which is close to the clip. This allows a head-neck coil terminating in the area of the section 8 to be positioned easily, overlapping the very narrow section 8 without any positioning problems being caused by the hearing protection 1 which is worn. The sections 8, 9 are essentially plane, apart from a minimal external curvature. The depth (corresponding to the width in the front view) of the lower section 8, including a slight curvature if applicable, is e.g. between 0.7 and 1 cm, while the depth of the upper section 9, including a slight curvature if applicable, is e.g. between 1.7 and 2.3 cm. In addition to the illustrated embodiment, of course, the overall outer shell can also be designed to have a planeness or depth which is essentially uniform, and therefore does not have to be divided into a narrower and a wider section. In order to minimize the lateral structural depth, the depth would preferably be approximately 1 cm again, preferably lying between 0.5 and 1.5 cm.

The hinge mounting of the two holding forks 4 takes place via pivot pins 10 which are molded on the outer shell 5 and onto which the relevant holding fork is snapped using corresponding snap-in holes. The front pivot pin 10 which is illustrated in FIG. 1 is designed as a hollow pin and serves as a connector for an acoustic tube 11 in each case, said acoustic tubes being linked via a connection piece 12 to a central acoustic tube 13 which leads to a sound source or similar. Each acoustic tube 11 can readily be pulled out of the acoustic connector at the relevant pivot pin 10. The hollow pivot pin 10 leads into a duct 14 which is provided in the inner part and itself terminates in a cavity 15 in the inner part, said cavity being funnel-shaped and opening out towards the ear of the patient. This is described in greater detail below.

Figure 2:
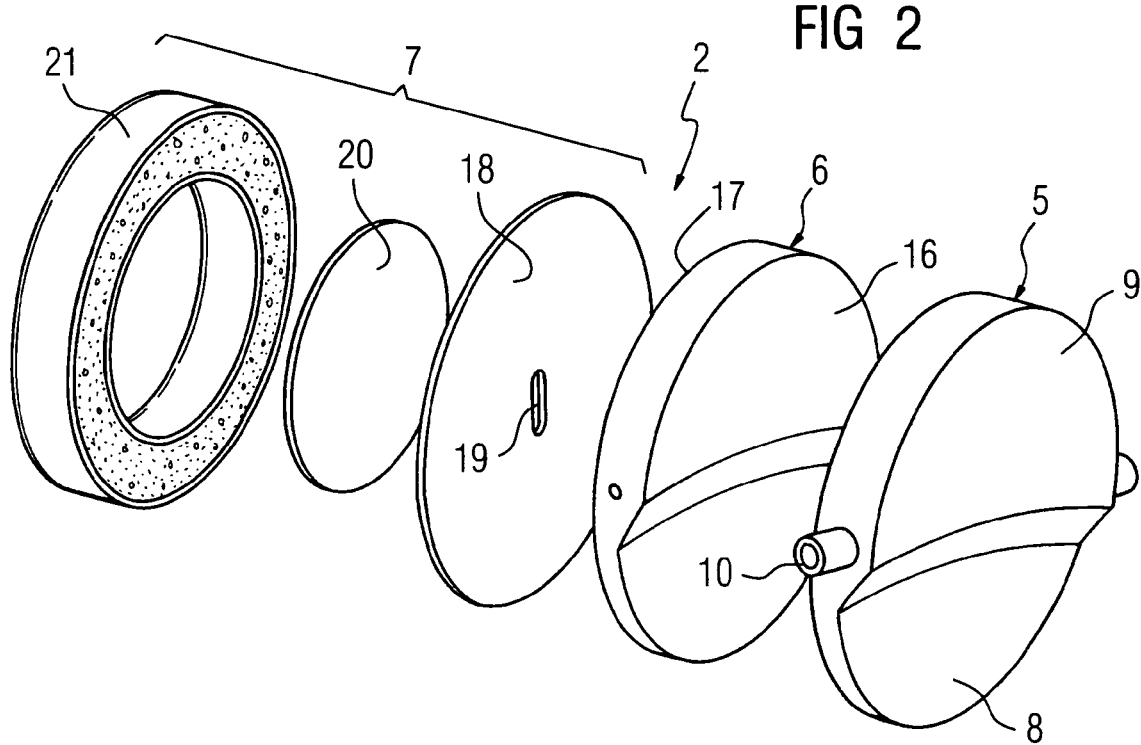
FIG. 2 shows an exploded representation of the individual components of an ear cover of the hearing protection from FIG. 1.
Figure 3:
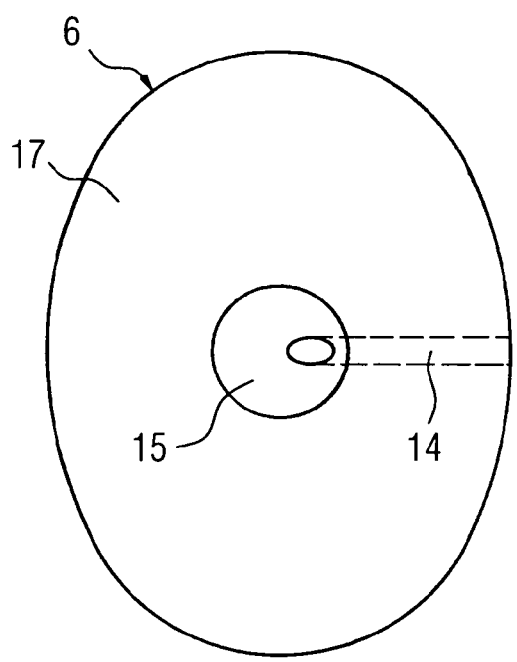
FIG. 3 shows a view of the surface of the inner part of the cover from FIG. 2, said surface being that which is oriented towards the ear of the patient.

FIG. 2 shows the individual parts of a cover 2 in the form of an exploded view. The outer shell 5 and the inner part 6 are shown as described, wherein that surface 16 of the inner part 6 which faces the inner surface of the outer shell 5 clearly corresponds to the inner surface contour of the outer shell 5, such that it can be positively inserted in a custom-fit manner. Both are preferably made of the same plastic, primarily of a polycarbonate or a polystyrene, wherein substances which cause minimal artifact formation in the magnetic resonance image should be utilized. In order to attach the inner part 6 in the outer shell 5, these being injection molded parts in each case, the contacting surfaces are preferably dissolved using a solvent and welded together in this manner. It is also conceivable to coat the outer shell 5 onto the previously manufactured inner part 6, this being readily possible if identical plastics are utilized. Correspondingly, the inner part 6 can also be injected into the previously molded outer shell 5. In each case, it must be taken into consideration that the inner part 6 is as dense as possible, and therefore a minimal pore volume is established. Therefore the inner part 6 must be as compact as possible, since the attenuation effect in the claimed hearing protection is achieved by means of the mass which is placed in front of the ear, said mass consisting of plastic outer shell 5 and inner part 6. With reference to the bond between inner part 6 and outer shell 5, it must be ensured that this excludes to the greatest possible extent any inclusion of air bubbles, etc., thereby preventing the formation in the bonding area of any resonance points which could possibly result in artifact formation.

As described above, the ear pad 7 is preferably adhered to that side 17 of the inner part 6 which faces the patient. As per FIG. 2, the ear pad 7 itself consists of a mounting 18, e.g. a sufficiently stable plastic film or plastic disc, which has a central perforation 19, said perforation being an elongated hole in this case, wherein this perforation is positioned such that it lies over the cavity 15 in the inner part 6 following assembly. A vibrating membrane, e.g. a plastic film, is adhered onto that side of the mounting 18 which is opposite to the inner part 6. This completely covers the perforation 19. Finally, an annular pad 21 which fits closely onto the head of the patient and seals the cover against the head is adhered to the mounting. The ear pad 7 is simply adhered to the inner part 6 as a ready-made part during assembly. Instead of using a separate vibrating membrane 20, this can also be part of the coating which envelopes the foam part in the interior of the annular pad 21.

Figure 4:
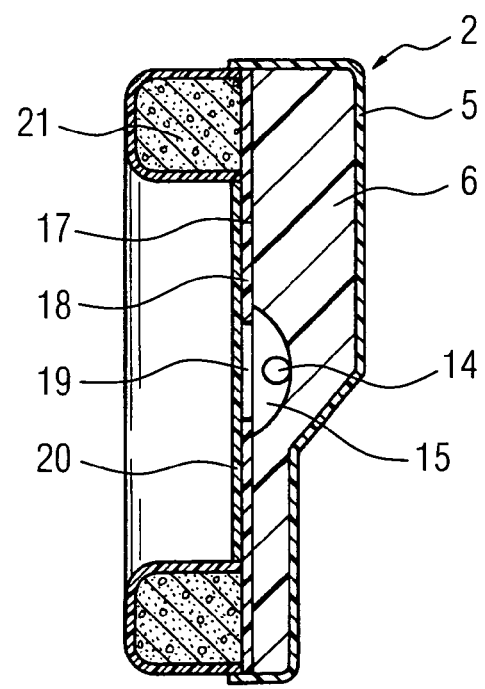
FIG. 4 shows a sectional view through an assembled cover.

FIG. 4 shows a sectional view through a cover 2. It shows firstly the plastic outer shell 5 and the inner part 6 which is positively fitted within it. It also shows the funnel-shaped cavity 15 and the duct 14 which opens into it, said duct being connected to the hollow pivot pin 10 on the outer shell 5. Also shown are the mounting 18 which is adhered onto the inner part 6, and its perforation 19 which clearly lies over the cavity 15. The perforation 19 and the cavity 15 alike are covered by the membrane 20 which can vibrate. The annular pad 21 is also shown.

If acoustic information, whether music or an instruction to the patient, is now provided via the central acoustic tube 13, the sound pressure varies in the acoustic tube 13 and in the acoustic tubes 11. This sound pressure is carried via the hollow pivot pin 10 into the duct 14 in the inner part, where it emerges into the cavity 15. As a result of the pressure change, the membrane 20 vibrates, whereby the sound pressure is transmitted to the air volume which lies behind the vibrating membrane 20 and is encapsulated by the annular pad 21, and is carried to the ear of the patient. Excellent acoustic perceptibility can therefore be achieved in respect of the acoustic information which is provided.

The invention claimed is:

1. A hearing protection device for use in magnetic resonance facilities, comprising:
    two protective covers for covering the ears of an examination patient and the protective covers being connected to each other via a clip and each protective cover having a plastic outer shell; and a compact inner part arranged in and permanently connected to the outer shell,
    wherein the inner part consists of a dimensionally stable solid plastic mass and essentially filling the outer shell completely,
    wherein a connector for an acoustic tube is provided at a front or rear end face of the outer shell and the connector is connected to a duct which passes through the inner part and leads to an inner part surface that faces the ear of the examination patient.

2. The hearing protection device according to claim 1, wherein the plastic outer shell, when viewed from the front, is narrower in a lower section that is remote from the clip than in the adjoining upper section that is close to the clip.

3. The hearing protection device as claimed in claim 1, wherein a surface of the inner part that contacts the outer shell corresponds to the inner surface contour of the outer shell.

4. The hearing protection device as claimed in claim 1, wherein the outer shell is adhered or welded to the inner part, or the outer shell is coated onto the inner part, or the inner part is injected into the outer shell.

5. The hearing protection device as claimed in claim 1, wherein the outer shell and the inner part are made of the same plastic.

6. The hearing protection device as claimed in claim 1, wherein the outer shell and the inner part are made of a polycarbonate or a polystyrene.

7. The hearing protection device as claimed in claim 1, wherein a plurality of pivot pins project from and are molded onto the outer shell and a holding fork on the clip side is supported on the pivot pins in a hinged manner.

8. The hearing protection device as claimed in claim 7, wherein one of the pivot pins is hollow and forms a connector.

9. The hearing protection device as claimed in claim 1, wherein the duct leads to a cavity in the surface of the inner part.

10. The hearing protection device as claimed in claim 9, wherein a vibrating membrane is provided opposite to a duct opening or the cavity and exposed to the ear of the examination patient.

11. The hearing protection device as claimed in claim 10, wherein the vibrating membrane is arranged on an ear pad that is permanently connected to the inner part.

12. The hearing protection device as claimed in claim 11, wherein the ear pad has a stable mounting that has a perforation and the perforation corresponds to the duct opening or the cavity and is covered by the vibrating membrane that is connected to the mounting.

13. The hearing protection device as claimed in claim 12, wherein the ear pad is adhered to the inner part via the mounting.

* * * * *